US00PP22997P3

(12) United States Plant Patent
Tsukahara

(10) Patent No.: US PP22,997 P3
(45) Date of Patent: Aug. 28, 2012

(54) ***PETUNIA* PLANT NAMED 'PBLRE32-0'**

(75) Inventor: Jun Tsukahara, Yame (JP)

(73) Assignee: Daiichi Engei Co. Ltd, Tokyo (JP)

( * ) Notice: Subject to any disclaimer, the term of this patent is extended or adjusted under 35 U.S.C. 154(b) by 14 days.

(21) Appl. No.: 12/930,869

(22) Filed: Jan. 19, 2011

(65) Prior Publication Data

US 2012/0185983 P1 Jul. 19, 2012

(51) Int. Cl.
*A01H 5/00* (2006.01)

(52) U.S. Cl. ..... Plt./356.23

(58) Field of Classification Search ..... Plt./356.23
See application file for complete search history.

*Primary Examiner* — Susan McCormick Ewoldt
(74) *Attorney, Agent, or Firm* — Cassandra Bright

(57) ABSTRACT

A new and distinct *Petunia* cultivar named 'PBLRE32-0' is disclosed, characterized by unique solid scarlet red flowers with white throat and a mounding plant habit. Plants of the new variety are highly floriferous and form dense, attractive plant shapes with exceptionally good branching. The new variety is a *Petunia*, suitable as an outdoor garden or container plant.

2 Drawing Sheets

Figure 1:
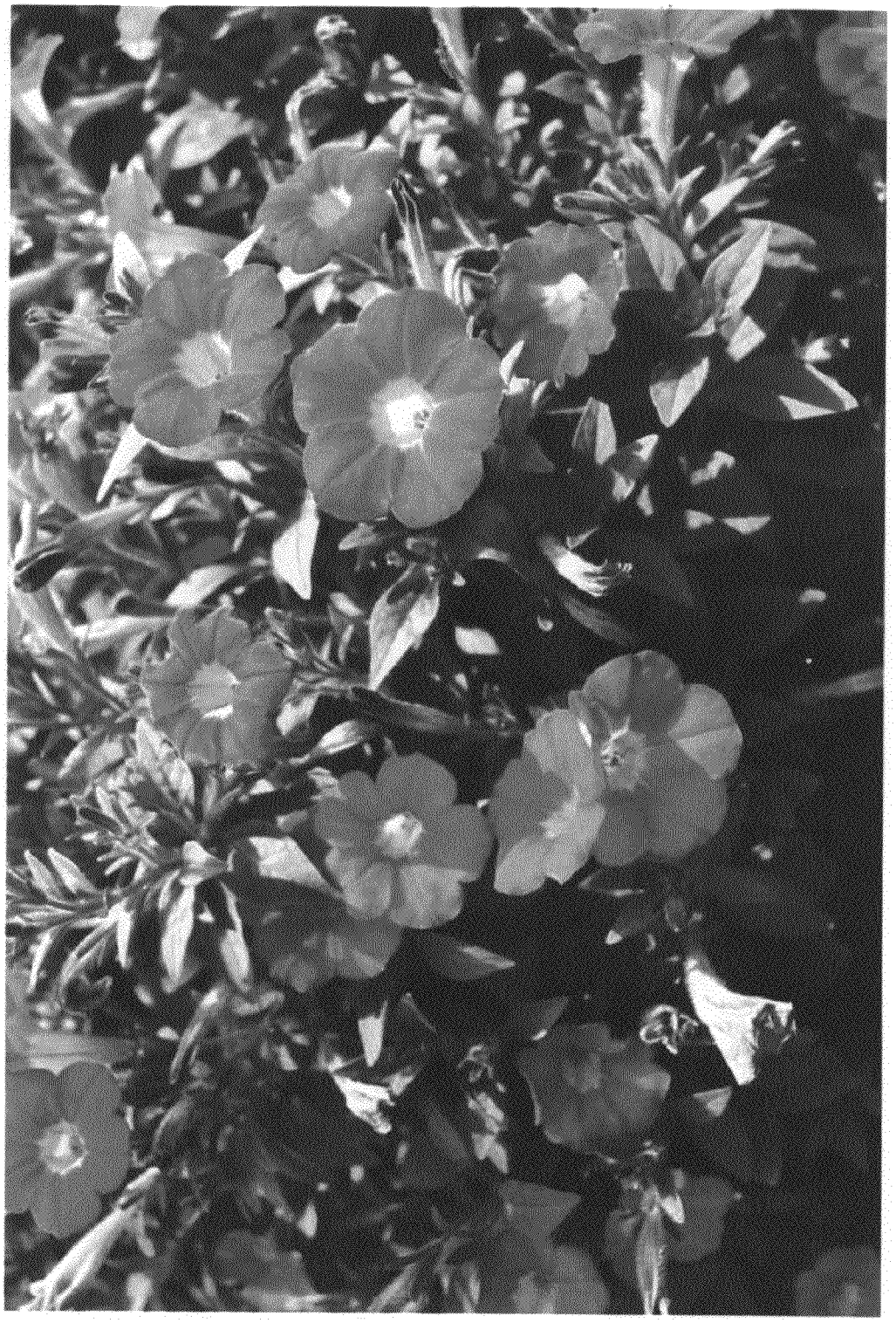

Latin name of the genus and species: *Petunia* hybrid.

Variety denomination: 'PBLRE32-0'.

The new *Petunia* cultivar resulted as part of a planned breeding program by the inventor Jun Tsukahara, in Yame, Fukuoka, Japan. The objective of the breeding program was to develop new *Petunia* varieties with interesting colors and attractive plant forms.

The new variety resulted from the crossing of the seed parent, an unnamed, unpatented proprietary *Petunia* seedling with the pollen parent, an unnamed, unpatented proprietary *Petunia* seedling in September 2006. The new variety was discovered in May of 2007 by the inventor in a group of seedlings resulting from that crossing, in a commercial greenhouse in Yame, Fukuoka, Japan.

Asexual reproduction of the new cultivar 'PBLRE32-0' by vegetative cuttings was first performed at a commercial greenhouse in Yame, Fukuoka, Japan in May 2007. Subsequently many generations have been produced and have shown that the unique features of this cultivar are stable and reproduced true to type.

SUMMARY OF THE INVENTION

The cultivar 'PBLRE32-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'PBLRE32-0.' These characteristics in combination distinguish 'PBLRE32-0' as a new and distinct *Petunia* cultivar:

1. Unique flower color of solid scarlet red with a white throat.
2. Mounding plant shape.
3. Highly floriferous plant habit.
4. Attractive densely growing plant habit.
5. Exceptionally good branching.

COMPARISON TO THE PARENT VARIETIES

Plants of the new cultivar 'PBLRE32-0' are similar in most horticultural characteristics to plants of the unnamed proprietary seed parent. However, the new variety has a larger overall flower size and shorter internodes than the seed parent. Additionally, plants of the seed parent produce red-violet colored flowers, whereas 'PBLRE32-0' produces scarlet red flowers.

Plants of the new cultivar 'PBLRE32-0' are similar in most horticultural characteristics to plants of the unnamed proprietary pollen parent. However, the pollen parent has darker colored flowers, and a larger overall flower size than the new cultivar. Additionally, the pollen parent has longer internodes and a less mounding plant habit than the new cultivar.

COMPARISON TO COMMERCIAL VARIETIES

The new cultivar can be compared to the patented commercial variety 'Blue Salmon Pink' U.S. Plant Pat. No. 18,181. 'PBLRE32-0' is similar to this commercial variety in most horticultural characteristics, most specifically, in plant habit, however, plants of the new variety produce different color flowers, and produce more flowers per plant.

The new cultivar can be compared to the patented commercial variety 'MP101' U.S. Plant Pat. No. 14,998. 'PBLRE32-0' is similar to this commercial variety in most horticultural characteristics, however, plants of the new variety produce larger flowers, and an overall plant shape that is significantly more mounding than trailing.

BRIEF DESCRIPTION OF THE PHOTOGRAPH

The accompanying photograph in FIG. 1 illustrates in full color typical flowers and foliage of 'PBLRE32-0'.

Figure 2:
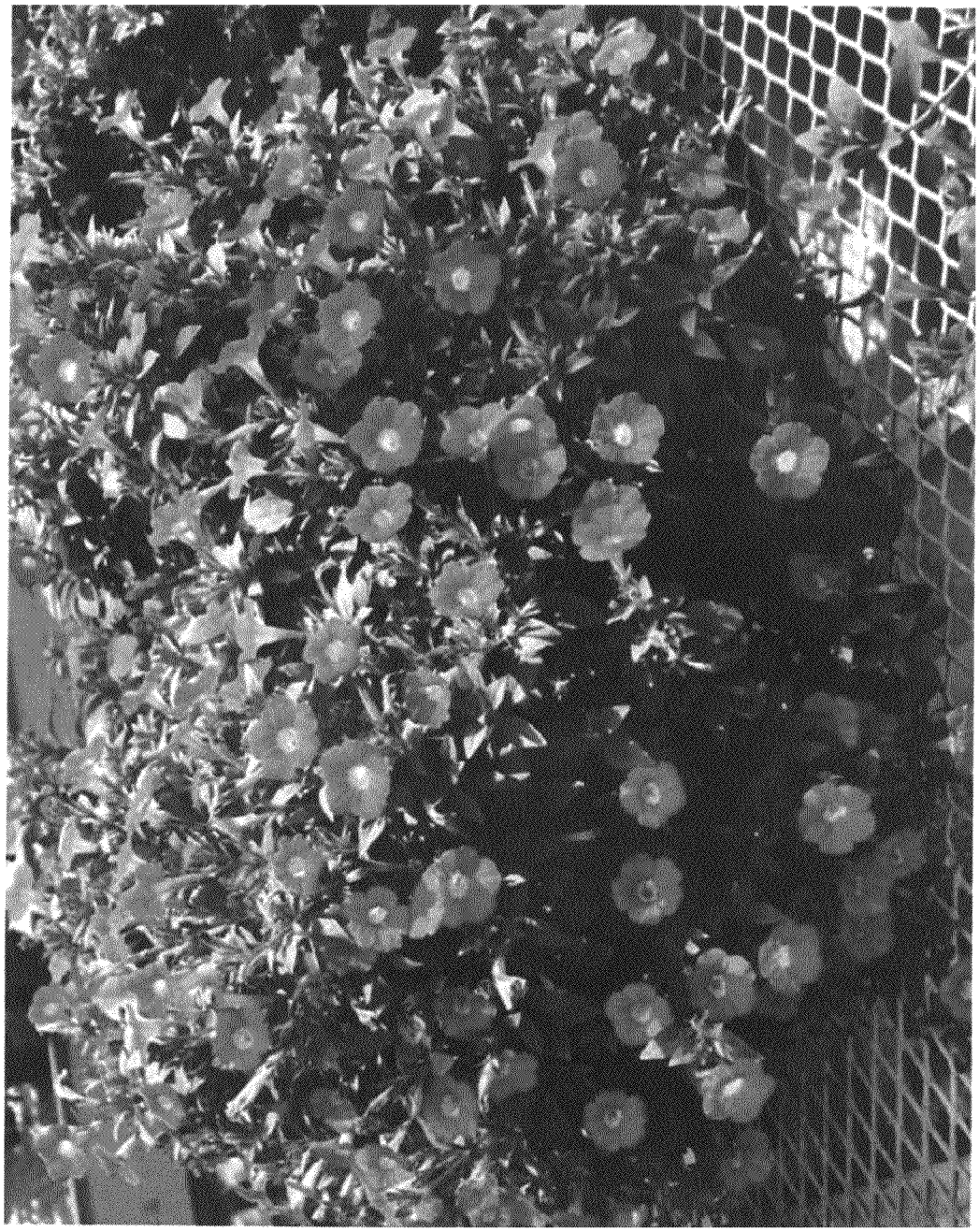

FIG. 2 illustrates a typical plant of 'PBLRE32-0' grown in a greenhouse, in a 10 inch commercial basket. Age of the plant photographed is approximately 20 weeks from 5 rooted cuttings. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurement describe 'PBLRE32-0' plants grown in a commercial greenhouse in Oxnard, Calif. The growing temperature ranged from 18° C. to 25° C. The greenhouse is subject to partial shade. General light conditions are bright, normal sunlight with some shade during the brightest part of the day. Measurements and numerical values represent averages of typical plant types.

Botanical classification: *Petunia* hybrid 'PBLRE32-0'.

PROPAGATION

Time to initiate roots: About 7 days at approximately 25° C.

Time to develop roots: About 14 to 21 days at approximately 25° C.

Root description: Fine, fibrous.

PLANT

Growth habit: Mounding.

Age of the plant described: Approximately 20 weeks from 5 rooted cuttings.

Pot size of plant described: Approximately 10 inch basket.

Height: Approximately 21 cm from soil line to top of plant.

Plant spread: Approximately 48 cm at widest point.

Growth rate: Rapid.

Branching characteristics: Free branching.

Length of primary lateral branches: Approximately 18 cm.

Quantity of primary lateral branches: Approximately 70.

Characteristics of primary lateral branches:

- *Diameter*.—Approximately 0.3 cm.
- *Color*.—Near RHS Green 138A.
- *Texture*.—Pubescent.
- *Strength*.—Highly flexible, moderately strong.

Internode length: Approximately 1.9 cm.

FOLIAGE

Leaf:

- *Arrangement*.—Opposite.
- *Quantity*.—Approximately 18 per main lateral branch.
- *Average length*.—Approximately 3.8 cm.
- *Average width*.—Approximately 1.5 cm.
- *Shape of blade*.—Oblanceolate.
- *Apex*.—Acute.
- *Base*.—Obtuse.
- *Margin*.—Entire.
- *Texture of top surface*.—Matte with pubescence.
- *Pubescence*.—Very short, less than 1 mm hairs, densely covering leaf.
- *Aspect*.—Very slightly recurved.
- *Color*.—Young foliage upper side: Near RHS Green 137A. Young foliage under side: Near RHS Green 137C. Mature foliage upper side: Near RHS Green 137C. Mature foliage under side: Near RHS Green 137D.
- *Venation*.—Type: Pinnate. Venation color upper side: Near RHS Yellow-Green 144B. Venation color under side: Near RHS Yellow-Green 144C.
- *Petiole*.—Length: Approximately 0.2 cm. Diameter: Approximately 0.1 cm. Color: Near RHS Green 137B. Texture: Pubescent.

FLOWER

Natural flowering season: Spring and Summer.

Days to flowering from rooted cutting: Approximately 50.

Inflorescence and flower type and habit: Single salverform with fused petals.

Rate of flower opening: Approximately 2 to 3 days from bud to fully opened flower.

Flower longevity on plant: Approximately 1 week.

Approximate quantity of flowers per plant: Approximately 200 flowers and buds.

Flowers: Persistent.

Bud:

- *Shape*.—Oblong.
- *Length*.—Approximately 3 cm.
- *Diameter*.—Approximately 1.4 cm.
- *Color*.—Near RHS Yellow-White 158B, distal end near Orange-Red N34A.

Flower size:

- *Diameter, widest point*.—Approximately 5 cm.
- *Overall length*.—Approximately 6.5
- *Flower tube length*.—Approximately 3.5 cm.
- *Flower tube diameter at distal end*.—Approximately 1.7 cm.
- *Flower tube diameter at proximal end*.—Approximately 0.8 cm.

Petals:

- *Length from throat*.—About 2 cm.
- *Width*.—About 2.5 cm.
- *Quantity*.—5, fused.
- *Texture*.—Smooth.
- *Apex*.—Truncate.
- *Margin*.—Entire.

Color:

- *When opening*.—Inner surface: Near RHS Orange-Red N34A. Outer surface: Near RHS Orange-Red N34C.
- *Fully opened*.—Inner surface: Near RHS Red 42A. Outer surface: Near RHS Red 36A. Flower throat (inside): Near RHS White N155B. Flower tube (outside): Near RHS Red 36D. Petal color, fading to: Near RHS Red 43B.

Calyx/sepals:

- *Quantity per flower*.—5, fused at base.
- *Shape*.—Oblong.
- *Length*.—Approximately 2.1 cm.
- *Width*.—Approximately 0.3 cm.
- *Apex*.—Acute.
- *Base*.—Fused.
- *Margin*.—Entire.
- *Texture*.—Pubescent.
- *Color*.—Upper Surface: Near RHS Green 137A. Lower Surface: Near RHS Green 137C.
- *Peduncle*.—Length: Approximately 1.8 cm. Diameter: Approximately 0.2 cm. Color: Near RHS Green 137A. Orientation: Approximately 45 degree angle from stem.

Fragrance: Sweet.

REPRODUCTIVE ORGANS

Stamens:

- *Number*.—5.
- *Filament length*.—Approximately 1.2 cm.

Anthers:

*Length*.—Approximately 0.1 cm.

*Shape*.—Globular.

*Color*.—RHS Greyed-Yellow 160B.

*Pollen*.—Not observed.

Pistil:

*Number*.—1.

*Length*.—Approximately 1.1 cm.

*Style*.—Length: Approximately 1 cm. Color: Near RHS White N155D.

*Stigma*.—Shape: Oblate. Color: Near RHS Green-White 157A. Ovary Color: Near RHS Yellow-Green 150D.

OTHER CHARACTERISTICS

Seeds and fruits: Not observed.

Disease/pest resistance: Neither resistant nor susceptible to normal diseases and pests of *Petunia*.

Temperature tolerance: The new variety tolerates temperatures between approximately 6° to 35° C.

What is claimed is:

1. A new and distinct cultivar of *Petunia* plant named 'PBLRE32-0' as herein illustrated and described.

* * * * *